(12) United States Patent
Albert et al.

(10) Patent No.: US 7,674,578 B2
(45) Date of Patent: Mar. 9, 2010

(54) METHODS OF USING SIP-10 TO ASSESS HCV CLEARANCE AND/OR RESPONSE TO INTERFERON THERAPY

(75) Inventors: Matthew Albert, Paris (FR); Jeremie Decalf, Paris (FR); Stanislas Pol, Juvisy sur Orge (FR); Arnaud Fontanet, Paris (FR); Mostafa Mohamed, Heliopolis Cairo (EG)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 11/855,238

(22) Filed: Sep. 14, 2007

(65) Prior Publication Data

US 2008/0119388 A1 May 22, 2008

Related U.S. Application Data

(60) Provisional application No. 60/844,375, filed on Sep. 14, 2006.

(51) Int. Cl.
*C12Q 1/00* (2006.01)
*G01N 33/53* (2006.01)

(52) U.S. Cl. .................... 435/4; 435/5; 435/7.1

(58) Field of Classification Search ............. None
See application file for complete search history.

(56) References Cited

U.S. PATENT DOCUMENTS 5,728,377 A 3/1998 Sarris et al.
2005/0282179 A1 12/2005 Martin et al.

FOREIGN PATENT DOCUMENTS

WO    WO 99/28474    6/1999

OTHER PUBLICATIONS

Apolinario et al., "Increased circulating and intrahepatic T-cell-specific chemokines in chronic hepatitis C: relationship with the type of virological response to peginterferon plus ribavirin combination therapy," Alimentary Pharmacology and Therapeutics, vol. 19 No. 5, pp. 551-562 (Mar. 2004).*

Buttmann et al., "TRAIL, CXCL10 and CCL2 plasma levels during long-term Interferon-β treatment of patients with multiple sclerosis correlate with flu-like adverse effects but do not predict therapeutic response," Journal of Neuroimmunology, vol. 190 Nos. 1-2, pp. 170-176 (Oct. 2007).*
Diago et al., "Association of pretreatment serum interferon gamma inducible protein 10 levels with sustained virological response to peginterferon plus ribavirin therapy in genotype 1 infected patients with chronic hepatitis C.," Gut, vol. 55 No. 3, pp. 374-37 (Epub Sep. 8, 2005).*
Firneisz et al. "Serum Dipeptidyl Peptidase IV (DPP IV, CD26) Activity in Chronic Hepatitis C.," Scandinavian Journal of Gastroenterology, vol. 36 No. 8, pp. 877-880 (Aug. 2001).*
Hayashi et al., "Antiviral therapy for chronic hepatitis C: past, present, and future," Journal of Gastroenterology, vol. 41, pp. 17-27 (2006).*
Narikawa et al., "CSF-chemokines in HTLV-I-associated myelopathy: CXCL10 up-regulation and therapeutic effect of interferon-α," Journal of Neuroimmunology, vol. 159 Nos. 1-2, pp. 177-182 (Feb. 2005).*
Romero et al., "Interferon (IFN)—γ—Inducible Protein—10: Association with Histological Results, Viral Kinetics, and Outcome during Treatment with Pegylated IFN-α2a and Ribavirin for Chronic Hepatitis C Virus Infection," Journal of Infectious Diseases, vol. 194 No. 7, pp. 895-903 (Oct. 2006,Epub Aug. 29, 2006).*
Umezawa, Journal of Antibiotics, 1984, 37(4), pp. 422-425.
Callebaut et al, Science, 1993, 262, pp. 2045-2050.
Lim et al, Journal of Leukocyte Biology, 2005, 78, pp. 442-452.
McIntosh et al, Regulatory Peptides, 2005, 128, pp. 159-165.
Liao et al, J. Microbiol. Immunol. Infect., 2004, 37, pp. 67-70.
Proost et al, Blood, 2001, 98(13), pp. 3554-3561.
Andrieu et al, Journal of Clinical Virology, 2003, 27, pp. 59-68.
De Meester et al, Immunology Today, 1999, 20(8), 367-375.
Butera et al, Blood, 2005, 106(4), pp. 1175-1182.
Harvey et al, Journal of Leukocyte Biology, 2003, 74, pp. 360-369.
Arai et al, Cellular Immunology, 2002, 219, pp. 48-56.

\* cited by examiner

*Primary Examiner*—Zachariah Lucas
(74) *Attorney, Agent, or Firm*—Oblon, Spivak, McClelland, Maier & Neustadt, L.L.P.

(57) ABSTRACT

The present invention relates to methods for evaluating and predicting clinical outcomes in patients by measuring levels of sIP-10 protein expression as well as therapies using sIP-10 and its fragments.

5 Claims, 6 Drawing Sheets

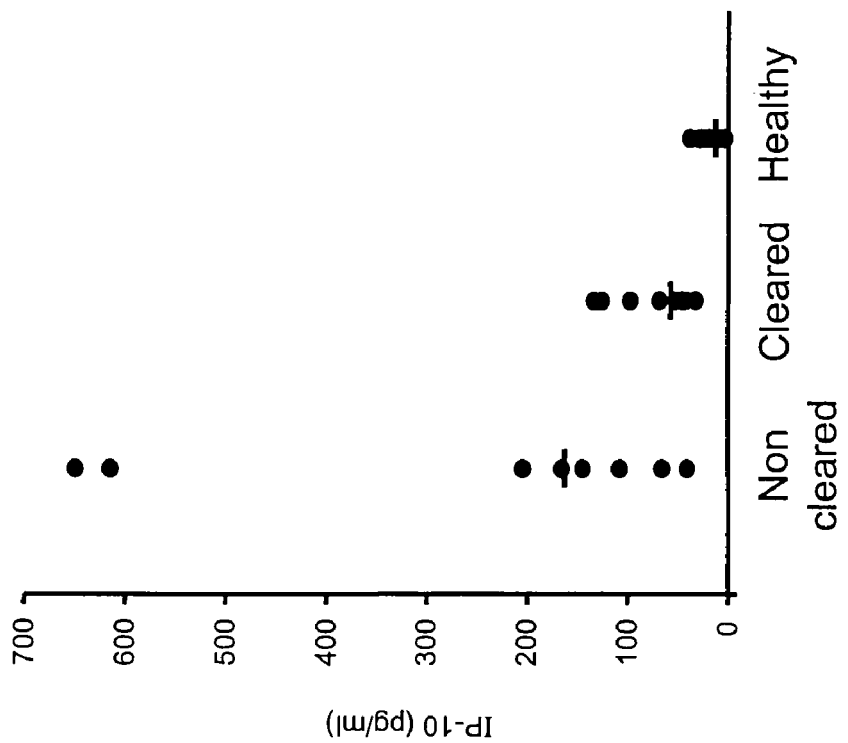
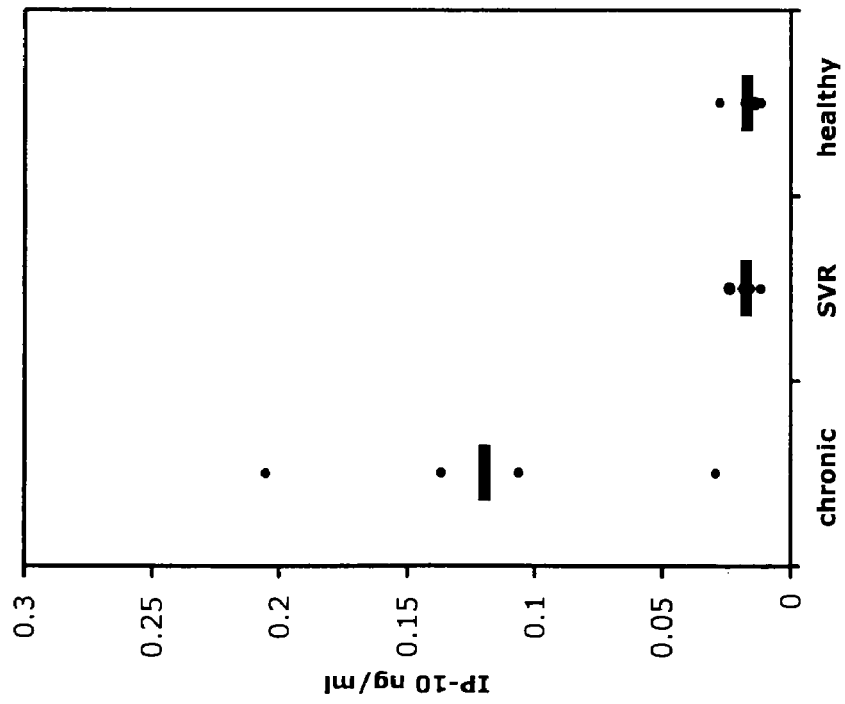

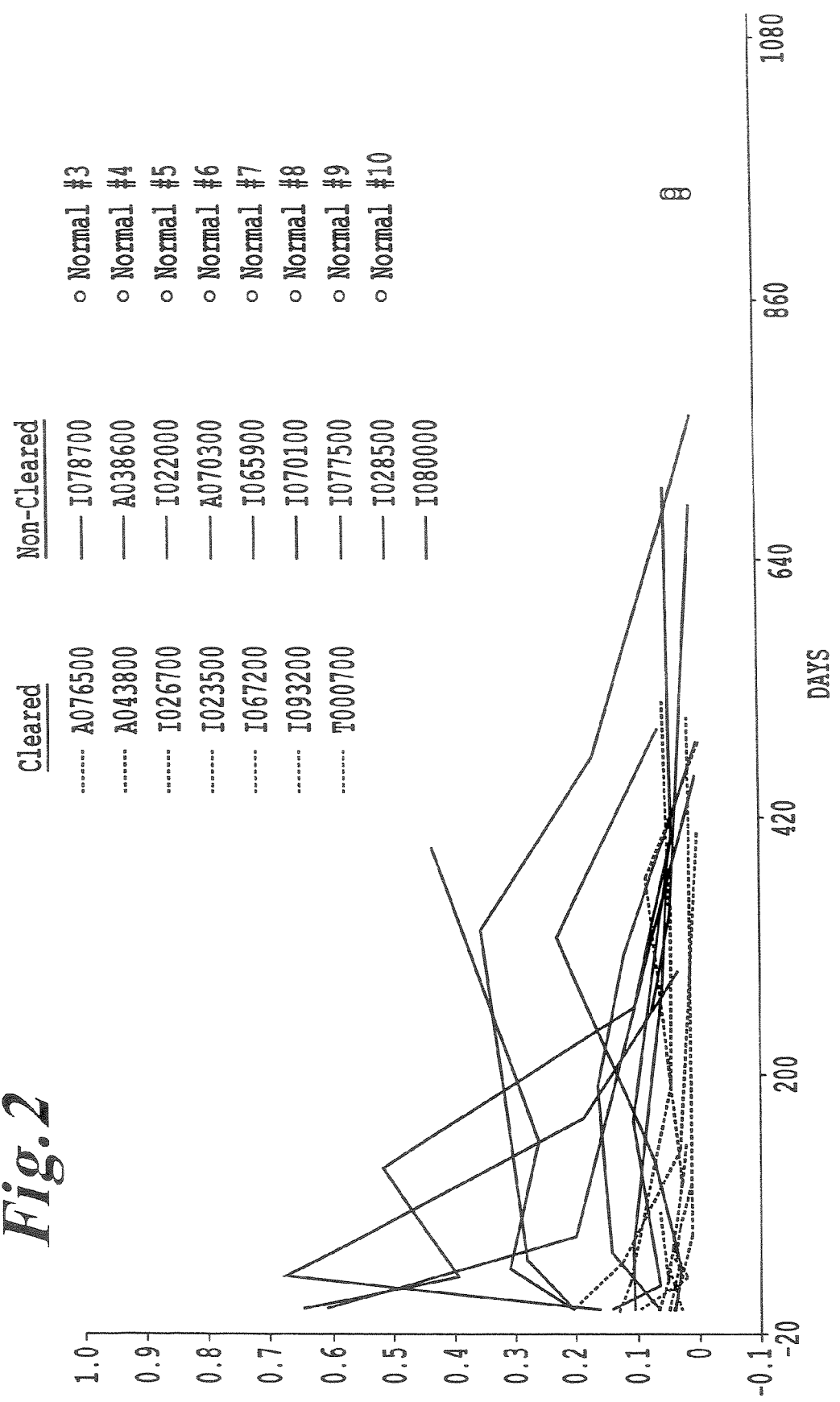

| Patients | IP-10 (ng/ml) |
|---|---|
| Healthy | |
| b280 | 0.02 |
| b281 | 0.02 |
| Chronic | |
| SM150305 | 0.029 |
| PD101005 | 0.205 |
| SVR | |
| PN010605 | 0.0236 |
| KP080405 | 0.0116 |

FIG. 3

SEQUENCE LISTING

<160> NUMBER OF SEQ ID NOS: 6

<210> SEQ ID NO 1
<211> LENGTH: 98
<212> TYPE: PRT
<213> ORGANISM: Homo sapiens
<220> FEATURE:
<221> NAME/KEY: mat_peptide
<222> LOCATION: (22)..(98)
<223> OTHER INFORMATION: Pro-IP-10

<400> SEQUENCE: 1

Met Asn Gln Thr Ala Ile Leu Ile Cys Cys Leu Ile Phe Leu Thr Leu
    -20                 -15                 -10

Ser Gly Ile Gln Gly Val Pro Leu Ser Arg Thr Val Arg Cys Thr Cys
 -5              -1   1               5                  10

Ile Ser Ile Ser Asn Gln Pro Val Asn Pro Arg Ser Leu Glu Lys Leu
            15                  20                  25

Glu Ile Ile Pro Ala Ser Gln Phe Cys Pro Arg Val Glu Ile Ile Ala
        30                  35                  40

Thr Met Lys Lys Lys Gly Glu Lys Arg Cys Leu Asn Pro Glu Ser Lys
    45                  50                  55

Ala Ile Lys Asn Leu Leu Lys Ala Val Ser Lys Glu Met Ser Lys Arg
60                  65                  70                  75

Ser Pro

<210> SEQ ID NO 2
<211> LENGTH: 77
<212> TYPE: PRT
<213> ORGANISM: Homo sapiens
<220> FEATURE:
<221> NAME/KEY: MISC_FEATURE
<222> LOCATION: (1)..(77)
<223> OTHER INFORMATION: Secreted full length IP-10 protein

<400> SEQUENCE: 2

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Met Ser Lys Arg Ser Pro
65                  70                  75

<210> SEQ ID NO 3
<211> LENGTH: 75
<212> TYPE: PRT
<213> ORGANISM: Homo sapiens
<220> FEATURE:
<221> NAME/KEY: MISC_FEATURE
<222> LOCATION: (1)..(75)
<223> OTHER INFORMATION: Secreted IP-10 protein lacking 2 N-terminal
      amino acids

<400> SEQUENCE: 3

Leu Ser Arg Thr Val Arg Cys Thr Cys Ile Ser Ile Ser Asn Gln Pro
1               5                   10                  15

-continued

Val Asn Pro Arg Ser Leu Glu Lys Leu Glu Ile Ile Pro Ala Ser Gln
            20                  25                  30

Phe Cys Pro Arg Val Glu Ile Ile Ala Thr Met Lys Lys Lys Gly Glu
        35                  40                  45

Lys Arg Cys Leu Asn Pro Glu Ser Lys Ala Ile Lys Asn Leu Leu Lys
    50                  55                  60

Ala Val Ser Lys Glu Met Ser Lys Arg Ser Pro
65                  70                  75

<210> SEQ ID NO 4
<211> LENGTH: 73
<212> TYPE: PRT
<213> ORGANISM: Homo sapiens
<220> FEATURE:
<221> NAME/KEY: MISC_FEATURE
<222> LOCATION: (1)..(73)
<223> OTHER INFORMATION: Secreted IP-10 protein lacking 4 N-terminal
      amino acid

<400> SEQUENCE: 4

Arg Thr Val Arg Cys Thr Cys Ile Ser Ile Ser Asn Gln Pro Val Asn
1               5                   10                  15

Pro Arg Ser Leu Glu Lys Leu Glu Ile Ile Pro Ala Ser Gln Phe Cys
            20                  25                  30

Pro Arg Val Glu Ile Ile Ala Thr Met Lys Lys Lys Gly Glu Lys Arg
        35                  40                  45

Cys Leu Asn Pro Glu Ser Lys Ala Ile Lys Asn Leu Leu Lys Ala Val
    50                  55                  60

Ser Lys Glu Met Ser Lys Arg Ser Pro
65                  70

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Val Pro Leu Ser Arg Thr Val Arg Cys
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Leu Ser Arg Thr Val Arg Cys
1               5

METHODS OF USING SIP-10 TO ASSESS HCV CLEARANCE AND/OR RESPONSE TO INTERFERON THERAPY

CROSS-REFERENCE TO RELATED APPLICATION

This application claims benefit of provisional application 60/844,375, filed Sep. 14, 2006.

BACKGROUND OF THE INVENTION

1. Field of the Invention

The present invention relates to methods for evaluating and predicting clinical outcomes in patients by measuring levels of protein expression as well as therapies using sIP-10 and its fragments.

2. Description of the Background

Hepatitis C virus (HCV) is a significant health problem in that chronic hepatitis occurs in about many HCV infected patients and may lead to the development of hepatic cancer. Chronic hepatitis is often treated with interferon $\alpha$ and/or $\beta$ with varying levels of success.

Even with interferon therapies, there are substantial side effects, and the costs of therapy are very high. Accordingly, there is a need to develop a way to assess when successful results can be expected in an individual patient with a particular IFN therapy.

Thus, an object of the invention is to provide a way in which to predict whether such therapies would be useful for treating certain patients.

SUMMARY OF THE INVENTION

There exists a need to determine and predict clinical outcomes in patients with HCV. It is therefore an object of the invention to provide a means for evaluating (e.g., determining and/or predicting) clinical outcome for a patient suffering from a clinical condition or syndrome, comprising the steps of (a) providing a clinical specimen obtained or derived from the patient, (b) measuring the levels of expression of a pre-selected set of proteins in the clinical specimen; and (c) comparing said levels of expression against a set of reference expression levels, where a deviation of the level of expression of one or more of the pre-selected set of proteins is indicative of clinical outcome for the patient.

BRIEF DESCRIPTION OF THE DRAWINGS

The patent or application file contains at least one drawing executed in color. Copies of this patent or patent application publication with color drawing(s) will be provided by the office upon request and payment of the necessary fee.

A more complete appreciation of the invention and many of the attendant advantages thereof will be readily obtained as the same becomes better understood by reference to the following detailed description when considered in connection with the accompanying drawings, wherein:

FIGS. 1A-B show the IP-10 levels in Paris Cohort (A)/Cairo (B) at the onset.

FIG. 2 shows the IP-10 acute patients (no treatment).

FIG. 3 shows CXCR3 expression in HCV patients.

DETAILED DESCRIPTION OF THE INVENTION

Unless specifically defined, all technical and scientific terms used herein have the same meaning as commonly understood by a skill artisan in chemistry, biochemistry, cellular biology, molecular biology, and medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. Further, the materials, methods, and examples are illustrative only and are not intended to be limiting, unless otherwise specified.

The phrase "pre-selected gene(s)" refers to proteins that have been determined to be suitable in practice of the invention. Preferably, in accordance with practice of the invention, such proteins are selected where there is a correlation between the level of protein expression and the nature and extent of a disease state or other undesired condition.

Methods are provided for quantitating protein expression levels, and the measured levels are compared against reference populations. Deviations from the reference levels can be correlated with clinical outcomes. For example, the type and extent of a patient's response to a therapeutic intervention can be determined, or the prognosis for a patient's survival can be estimated. The protein levels can be measured in essentially any chosen body tissue or fluid.

sIP-10 is implicated in the failure of chronically infected HCV patients to respond to interferon therapy. Additional applications may include evaluation of patients with chronic inflammation (e.g. cancer, obesity, autoimmunity, graft vs. host disease). Specific applications should be focused on diseases in which IP-10 and/or CD26 have been shown to be elevated (e.g., melanoma, type II diabetes, autoimmune vasculitis).

Specifically, the inventors have analyzed the relationships of IP-10 and HCV and have discovered that IP-10 is a negative predictive marker for clearance of hepatitis C virus (HCV). This has been demonstrated in a cohort of acute HCV patients with genotype 4 virus (Egyptian cohort, FIG. 1, 2) and a cohort of chronically infected HCV patients with genotype 1 virus (Paris cohort, FIG. 1). Notably, the latter study compared chronically infected patients and sustained virologic responders, but data from other groups (Butera et al, Blood 106(4):1175 (2005)) support the inventors' findings. This observation has been confusing for the field as it is counter-intuitive—IP-10 is considered a pro-inflammatory molecule and should facilitate the efficient priming of anti-HCV specific T cells.

Figure 4:
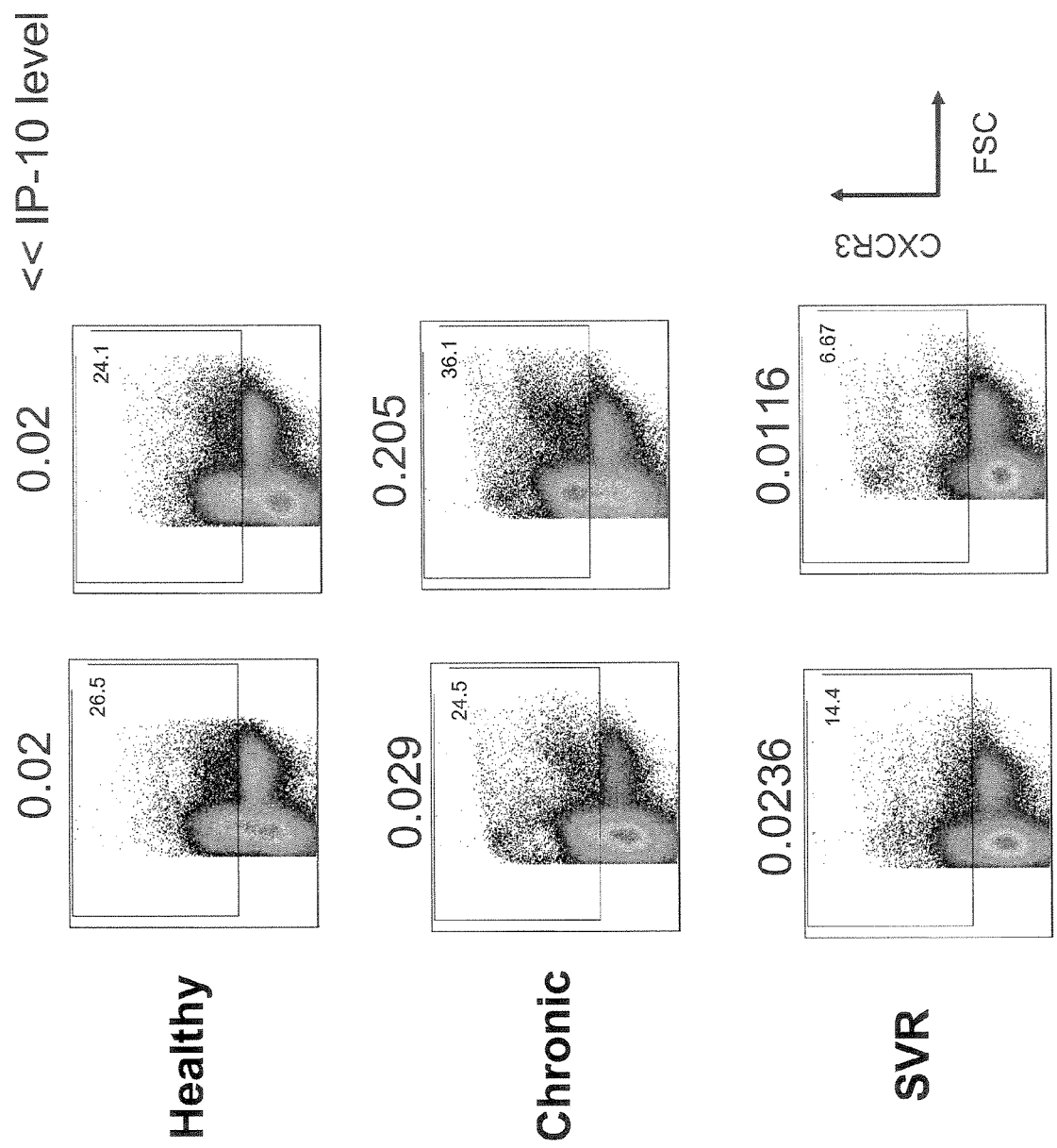
FIG. 4 shows CXCR3 expression on PBMCs.
Figure 5:
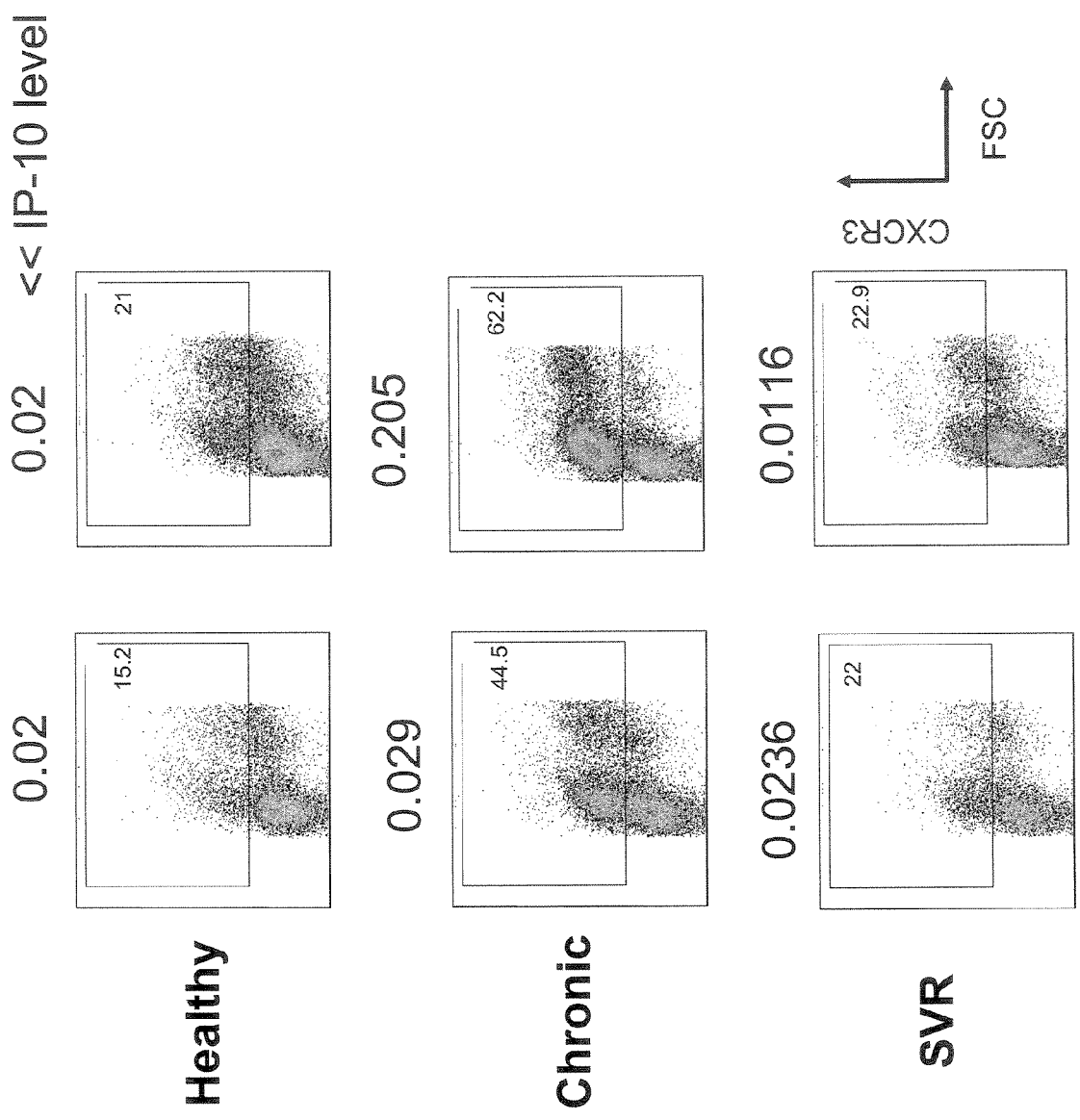
FIG. 5 shows CXCR3 expression on B cells.

Thus, the invention and the solution to this problem are based on the identifying by the inventors a positive correlation between the IP-10 levels in patients and the absolute number of CXCR3 positive cells in circulation (FIG. 3-5). This too was at first counter-intuitive as high levels of IP-10 in the tissue should result in the homing of CXCR3 (the sole receptor for IP-10) and a depletion of CXCR3 positive cells from the blood. It has been suggested in the literature that IP-10 may be cleaved by CD26 (also called DPPIV, dipeptidyl peptidase IV), resulting in the generation of a short form of IP-10 (sIP-10) that acts as an antagonist of CXCR3 (De Meester et al, Immunology Today 20(8):367 (1999)). Thus, as used herein, it is understood that sIP-10 means a short form of IP-10 that has been cleaved by CD 26 and portions thereof. For example, as described herein below, sIP-10 is reported to have an amino acid sequence shown as SEQ ID NO:3. In another embodiment, the sIP-10 has the sequence of RTVRC TCISISNQPV NPRSLEKLEI IPASQFCPRV EIIAT- MKKKG EKRCLNPESK AIKNLLKAVS KEMSKRSP (SEQ ID NO:4). These sequences can be used as well as fragments thereof having at least 10, 15, 20, 25, 30, 35, 40, 45, 50, 55, 60, 65, 70 and 75 amino acids thereof, as well as all values and ranges there between.

Therefore, it is apparent that sIP-10 is a clinically important predictive marker for failure to clear HCV/and failure to respond to IFN therapy. This represents an important and medically useful discovery as we will have the ability to determine prior to treatment, which patients will fail therapeutic treatment, thus saving them from up to a year of an expensive treatment with significant side effects (e.g., major depression). Of note, ~50% of genotype 1 patients fail to clear virus in response to IFN therapy. Furthermore, the introduction of such a diagnostic tool may assist physicians in determining responsive patients, thus pushing them to treat earlier with potentially more impact in avoiding the long-term sequella of HCV (e.g. cirrhosis, hepatocellular carcinoma).

One embodiment of the invention is to assess the ability of a patient to clear HCV from circulation and/or the body. In another embodiment, the effectiveness of interferon therapy can be assessed.

According to these embodiments, it is possible to assess these indices by determining the expression levels of sIP-10. In these embodiments, one can assess the expression and effects by comparing the expression level of sIP-10 to a set of reference expression levels predictive of a patient's ability to clear HCV. Likewise, an increased expression of sIP-10 relative to a reference expression standard is indicative of a decreased ability to clear HCV.

Since the effectiveness of IFN therapy is not limited to an HCV infected patients the methods can be carried out in patients not infected or not known to be infected.

A patient not infected with HCV who may benefit from this methodology may be a patient with a disease in which IFN is a normal course of therapy as known in the art.

An "individual" or "patient" which may be subjected to the methodology described herein may be any of mammalian animals including human, dog, cat, cattle, goat, pig, swine, sheep and monkey. Humans are preferable.

A "sample" is a biological sample such as blood, serum, lymph, and tissue. The "sample" may also be pretreated, for example, by homogenization, extraction, enzymatic and/or chemical treatments as commonly used in the field.

The preparation and/or isolation of protenacious material from a sample for analysis are also well known in this field.

Measuring the levels of sIP-10 expression in a sample is easily undertaken by one knowledgeable in this field. Non-limiting examples include, western-blot analysis, ELISA assays, immuno-reactivity assays, column assays using fluorescence, antibodies and radiolabeled markers to detect. Automated manners of performing the analysis, for example, using a computer processor can also be used.

The inventors developed the first method of detecting long form of IP-10. No detection system to date has been described for the detection of long form IP-10 and the determination of the amount of sIP-10 in a sample. This novel tool supports a method for predicting responsiveness to therapy in chronically infected HCV patients. Other applications may exist. This new tool solves the problem of determining the ratio of long/short form of IP-10. It has immediate use in prospective observational study for developing predictive markers in HCV patients.

Therefore, in such therapeutic methods, inhibiting CD26 and/or providing a short form IP-10 as an agonist of full length IP10 is part of the invention. The polypeptides can be naturally obtained, obtained from recombinant sources and/or synthesized chemically, the procedures for which are known in the field. Administration can be any suitable route, for example, intravenously, intranasally, peritoneally, intramuscularly, orally and other conventional methods. An active compound can be mixed and/or carried with one or more liquid and/or solid pharmaceutically acceptable carriers, ingredients and/or excipients. As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. If necessary, the chimeric compounds can be co-administered with a solubilizing agent, such as cyclodextran.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., chimericcompounds) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Nucleic acid molecules encoding the chimeric compounds of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) PNAS 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The dosages can be assessed by the physician administrating the therapy taking into consideration factors such as weight, age, sex, race, severity of the infection and other prior, concurrent and/or future therapies.

EXAMPLES

Material and Methods

Paris cohort. Patients who developed chronic HCV (<<<chronic>>>) or cleared the infection after treatment (<<<SVR, sustained virological responders>>>) were recruited at the hospital Necker, Paris in collaboration with Pr. Stanislas POL.

Cairo cohort. Patients identified as acute HCV and were regularly followed for up to 2 years after diagnosis of the disease. At each visit blood collection was performed to bank plasma and cells.

Luminex technology. The luminex technology allows us to follow up to 25 analytes in a single plasma sample. It is a bead based sandwich ELISA that utilizes cytometric principles and permits the simultaneous analysis of up to 100 analytes while using a small amount of patient plasma or cell supernatent.

Flow cytometry. Thawed PBMCs from patients were stained with CXCR3-PE and CD19-fitc (BD) for 20 min. Cells were washed, fixed with 1% PFA and read on FACS-CALIBUR (BD).

IP-10 digestion western blot and mass spectrometry. Commercially available, recombinant IP-10 (Abcam) and CD26 (Alexis Biochemical) were incubated for 1 h 30 at 37C. Samples were frozen for further analysis by mass-spectrometry or western blot. For western blot an anti-IP-10 monoclonal antibody (clone 4D5, Abcam) were used to detect both naïve and truncated molecules. Antibody was incubated 2 h at room temperature.

```
IP-10 AA sequence
Pro-IP-10:
                                           (SEQ ID NO:1)
MNQTAILICC LI FLTLSGIQ GVPLSRTVRC TCISISNQPV

NPRSLEKLEI IPASQFCPRV EIIATMKKKG EKRCLNPESK

AIKNLLKAVS KEMSKRSP

Secreted full length protein:
                                           (SEQ ID NO:2)
VPLSRTVRC TCISISNQPV NPRSLEKLEI IPASQFCPRV

EIIATMKKKG EKRCLNPESK AIKNLLKAVS KEMSKRSP

Cleavage product after CD26 treatment, as reported
in literature:
                                           (SEQ ID NO:3)
-LSRTVRC TCISISNQPV NPRSLEKLEI IPASQFCPRV

EIIATMKKKG EKRCLNPESK AIKNLLKAVS KEMSKRSP
```

FIG. 1: IP-10 as a predictor for clearance (A) Plasma obtained from healthy donors (N=6, right bars), chronic (N=4, left bars) and SVR (N=4, middle bars) were analyzed by LUMINEX (Biosource) for the presence of IP-10. Each point represents a unique patient, the bars are the average values. The concentrations are reported in ng/ml. (B) Serum samples from 7 cleared patients, 9 non cleared and 8 healthy donors were analyzed. Samples from HCV patients were collected during the acute phase of the disease. As above, IP-10 was measured by LUMINEX. Each dot represents a patient, the bars are the average values. Based on these results, we see that elevated IP-10 correlates with a failure to respond to IFNα treatment (A) and also to a patients' failure to spontaneously clear HCV during the acute phase of an infection (B). Based on this date, we and others have found IP-10 as a possible predictive marker for the evolution of HCV infection.

FIG. 2: IP-10 is elevated in patients developing a chronic disease

Serum samples from 7 patients who cleared the infection and 9 patients who developed chronic HCV were analyzed. Samples collection across the disease evolution started at the acute phase of the infection (PCR+ELISA−). IP-10 levels were evaluated using LUMINEX technology. Normal levels of IP-10 were evaluated by recruiting 8 healthy donors (grey dots). These result suggest that IP-10 is higher during the acute phase in patients that will develop a chronic form of the disease, and notably, it remains high all along the disease. In contrast, it is lower in patient who will clear the virus and after clearance, it returns to normal levels.

FIGS. 3, 4 & 5: Correlation between IP-10 levels and the expression of its receptor (3) IP-10 levels in 2 representative patients from each group are shown (Paris cohort)s: healthy, chronic and SVR. IP-10 levels were evaluated in plasma samples using the LUMINEX technology. (4) PBMCs isolated from 2 Healthy donors, 2 chronic patients and 2 SVR were stained with CXCR3-PE. Percentage of CXCR3+ cells among PBMCs were analyzed using flow cytometry. Corresponding IP-10 level measured in those patients is shown above each dot plot (ng/ml). (5) As B cells are known to express CXCR3, we followed CXCR3 expression on this subset using CD19 as specific marker for B cells. Corresponding IP-10 level measured in those patients is shown above each dot plot (ng/ml). These data suggest that the elevation of IP-10 levels in chronic patients positively correlates with the presence of CXCR3 expressing cells in the peripheral blood. As such, we interpret this data to mean that CXCR3$^+$ cells are actively being drawn into circulation as a result of the elevated IP-10. This is counter-intuitive and led to the hypothesis that IP-10 in HCV patients is cleaved, thus results in the generation of the antagonistic form—short IP-10 (sIP-10).

Figure 6A:
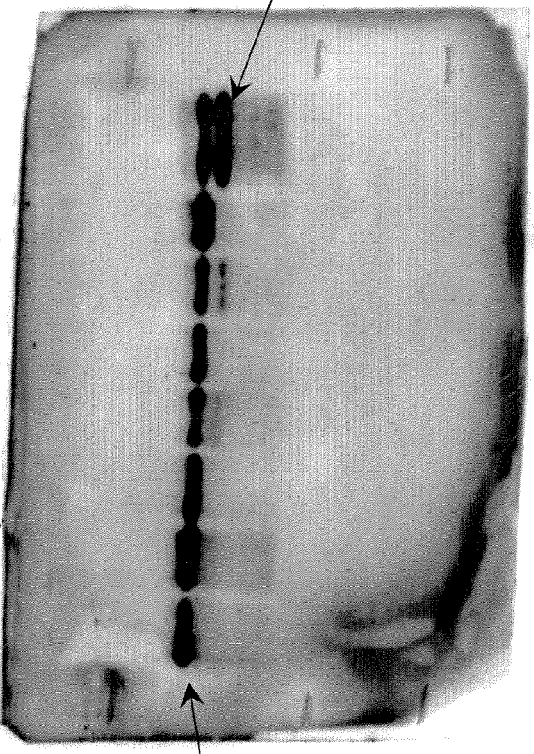
FIGS. 6(A) shows a western blot analysis of IP-10 with (+) and without (−) CD26; (B) shows mass spectroscopy analysis of IP-10.
Figure 6B:
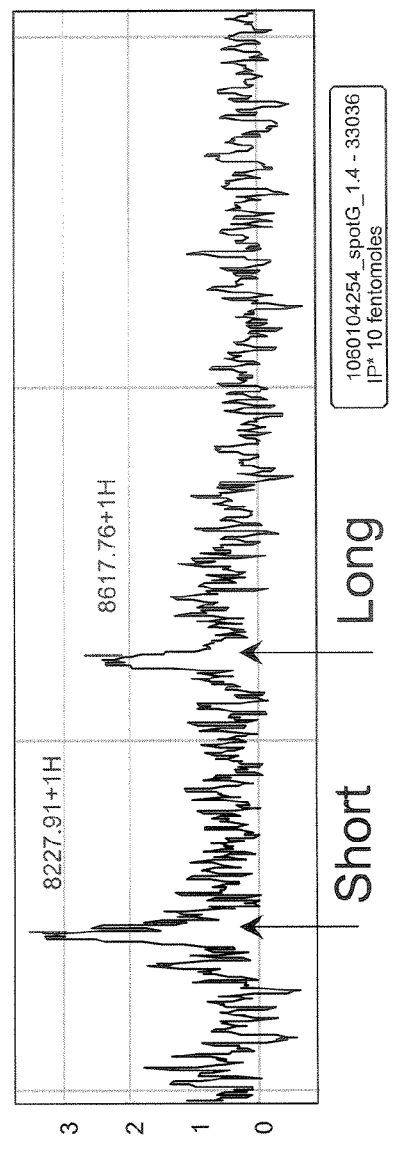

FIG. 6: short IP-10 is dominant in the plasma of HCV patients

It's been shown that IP-10 can be cleaved by 2 amino aids at its N-terminus. This short form (sIP-10) still binds its receptor but is not functional and can act as an inhibitor of IP-10 activity. We are currently developing assays to demonstrate that full length IP-10 is the wrong marker to follow and that in fact, sIP-10 is the predominant form in the plasma of HCV infected individuals. This should offer a much improved diagnostic test. To develop these assays we are using two recombinant proteins: human full length IP-10 expressed in *E.coli* and CD26 (DPPIV) an enzyme known to transform IP-10 to sIP-10 by cleaving the 2 N-termal amino-acids. We can generate long and short forms of IP-10 to validate an assay and establish a standard curve. After digestion, products are analyzed by western or mass-spectrometry that allows us to discriminate between full length and cleaved IP-10. FIG. 6 shows data of Western blot analysis (A) and mass spectrometry analysis (B). In the former, the upper band is full length IP-10 (MW=8.6 kDa) and the lower band corresponds to the cleaved form. Interestingly, using mass spectroscopy, the precise MW was determined. The two peaks represent full length IP-10 (MW=8.616 kDa) and a truncated short form (MW=8.220 kDa). Interestingly, this result suggest indicated that it is a 4 amino-acids (and not 2 amino-acids) cleavage event. The inventors show that they are able to discriminate between the two forms of IP-10. This assay can be validated with recombinant protein to detect IP-10 and sIP-10 in patients' plasma with a requirement for only a few microlitres of biological material.

Obviously, numerous modifications and variations of the present invention are possible in light of the above teachings. It is therefore to be understood that within the scope of the appended claims, the invention may be practiced otherwise than as specifically described herein.

The invention claimed is:

1. A method of assessing whether a hepatitis C virus (HCV) infected patient is likely to spontaneously clear the virus, the method comprising:

measuring an expression level of a short form of interferon-gamma-inducible protein 10 (sIP-10) in a sample from the patient during the acute stage of the HCV infection; and comparing the expression level of sIP-10 of the patient to an expression level of sIP-10 at the acute stage of a reference sample, thereby assessing the ability of the patient to clear the hepatitis C virus based on the expression level of sIP-10, wherein the HCV has genotype 1 or 4, the reference sample is derived at the acute stage of the infection from a group that thereafter spontaneously cleared the HCV infection, and an increased expression of sIP-10 relative to the expression of the reference sample is indicative of a decreased ability to clear the HCV.

2. The method of claim 1, wherein sIP-10 comprises at least 10 amino acids of SEQ ID NO:3.

3. The method of claim 2, wherein sIP-10 comprises SEQ ID NO:3.

4. The method of claim 1, wherein a decreased expression of sIP-10 relative to the expression of the reference sample is indicative of an increased ability to clear HCV.

5. The method of claim 1, which is automated.

* * * * *